US00PP29282P3

(12) United States Plant Patent
Klemm et al.

(10) Patent No.: US PP29,282 P3
(45) Date of Patent: May 8, 2018

(54) ***BEGONIA* PLANT NAMED 'KLEBG15006'**

(50) Latin Name: ***Begonia* spp.**
Varietal Denomination: KLEBG15006

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 16 days.

(21) Appl. No.: 14/999,822

(22) Filed: Jul. 5, 2016

(65) Prior Publication Data

US 2017/0295704 P1 Oct. 12, 2017

Related U.S. Application Data

(60) Provisional application No. 62/390,713, filed on Apr. 6, 2016.

(51) Int. Cl.
*A01H 5/02* (2018.01)

(52) U.S. Cl.
USPC ..... Plt./343
CPC ..... *A01H 5/0238* (2013.01)

(58) Field of Classification Search
USPC ..... Plt./343, 349
CPC ..... A01H 5/0238; A01H 5/02; A01H 5/00
See application file for complete search history.

(56) References Cited

PUBLICATIONS

Selecta Series Information Fiery Orange *Begonia* 2017, retrieved on Aug. 3, 2017, retrieved from the Internet at http://www.selectanorthamerica.com/series_info.aspx?phid=009500001022358, one page.*

Spring Trials 2015 Get the Inside Scoop, retrieved on Aug. 3, 2017, retrieved from the Internet at file:///C:/Users/jhwu/Downloads/15028_SpringTrialsBook_PAS_LR%20(1).pdf, cover page, pp. 31, 44, 46.*

Germania Seed Company 2015, retrieved on Aug. 8, 2017, retrieved from the Internet at https://www.germaniaseed.com/pdf/2016/2016_plant_EB_WEB.pdf, 5 pp. total including pp. 5, 74.*

* cited by examiner

*Primary Examiner* — June Hwu
(74) *Attorney, Agent, or Firm* — Bethany R. Roahrig; Barbara Campbell; Cochran Freund & Young LLC

(57) ABSTRACT

A new *Begonia* plant particularly distinguished by having orange-red colored flowers, double male flowers, and a semi-trailing form, is disclosed.

3 Drawing Sheets

Genus and species: *Begonia* spp.
Variety denomination: 'KLEBG15006'.

BACKGROUND OF THE NEW PLANT

The present invention comprises a new and distinct variety of *Begonia*, botanically known as *Begonia* spp. and hereinafter referred to by the variety name 'KLEBG15006'. 'KLEBG15006' resulted from a controlled cross-pollination conducted between June and July of 2011 in Stuttgart, Germany between female *Begonia* variety 'BG-2010-0090' (unpatented) and male *Begonia* variety 'BG-2010-0068' (unpatented). 'KLEBG15006' was selected in the spring of 2012 in Stuttgart, Germany.

In June of 2012 'KLEBG15006' was first vegetatively propagated by terminal cuttings. 'KLEBG15006' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Orange-red colored flowers;
2. Double male flowers; and
3. Semi-trailing form.

DESCRIPTION OF THE PHOTOGRAPH

This new *Begonia* plant is illustrated by the accompanying photographs which show an overall view of the plant. The colors shown are as true as can be reasonably obtained by conventional photographic procedures.

DESCRIPTION OF THE NEW VARIETY

Figure 1:
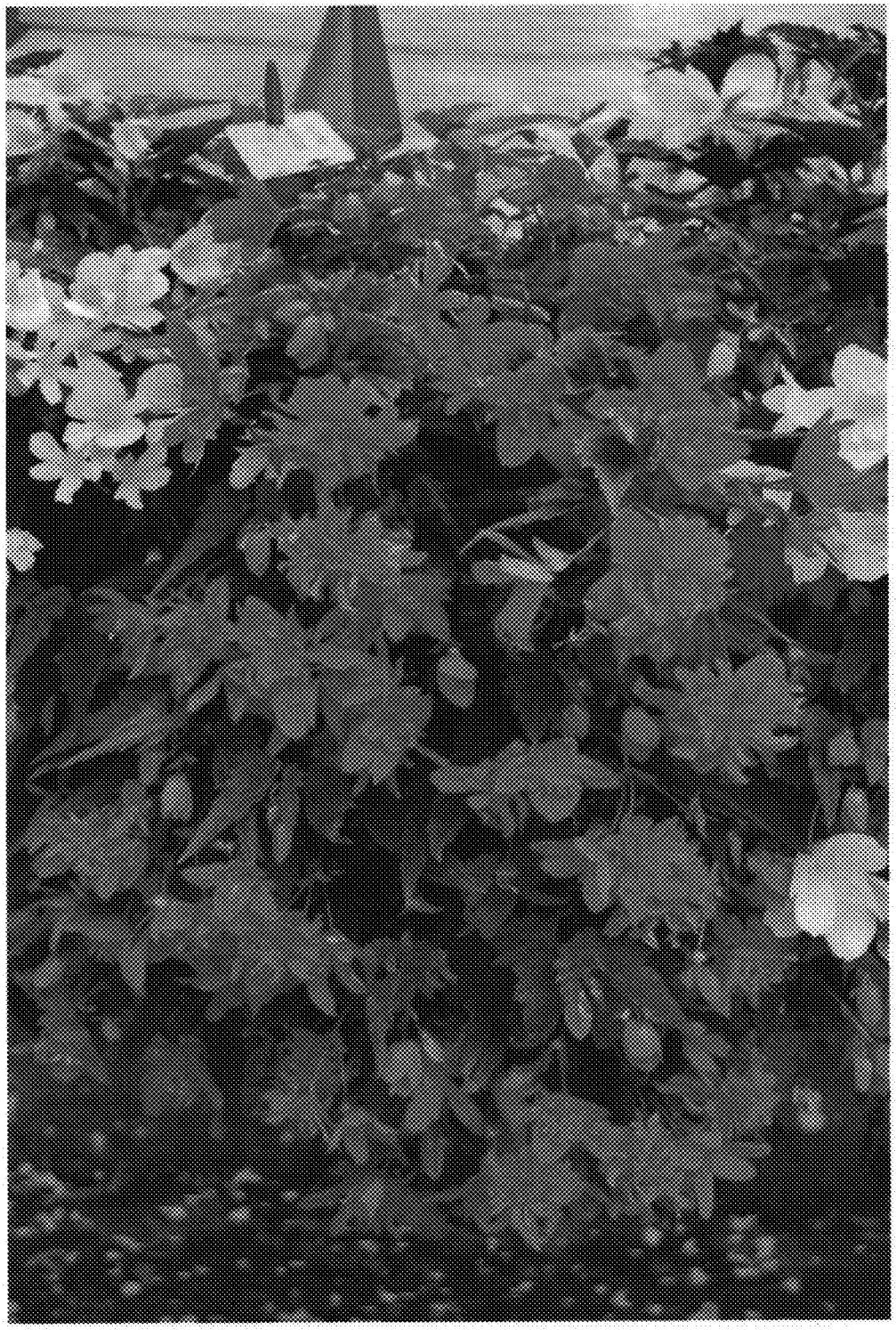
FIG. 1 shows a plant that is 16 weeks-old grown in a greenhouse in Stuttgart, Germany in August 2014. Other white *begonias* are pictured on the top and right sides.
Figure 2:
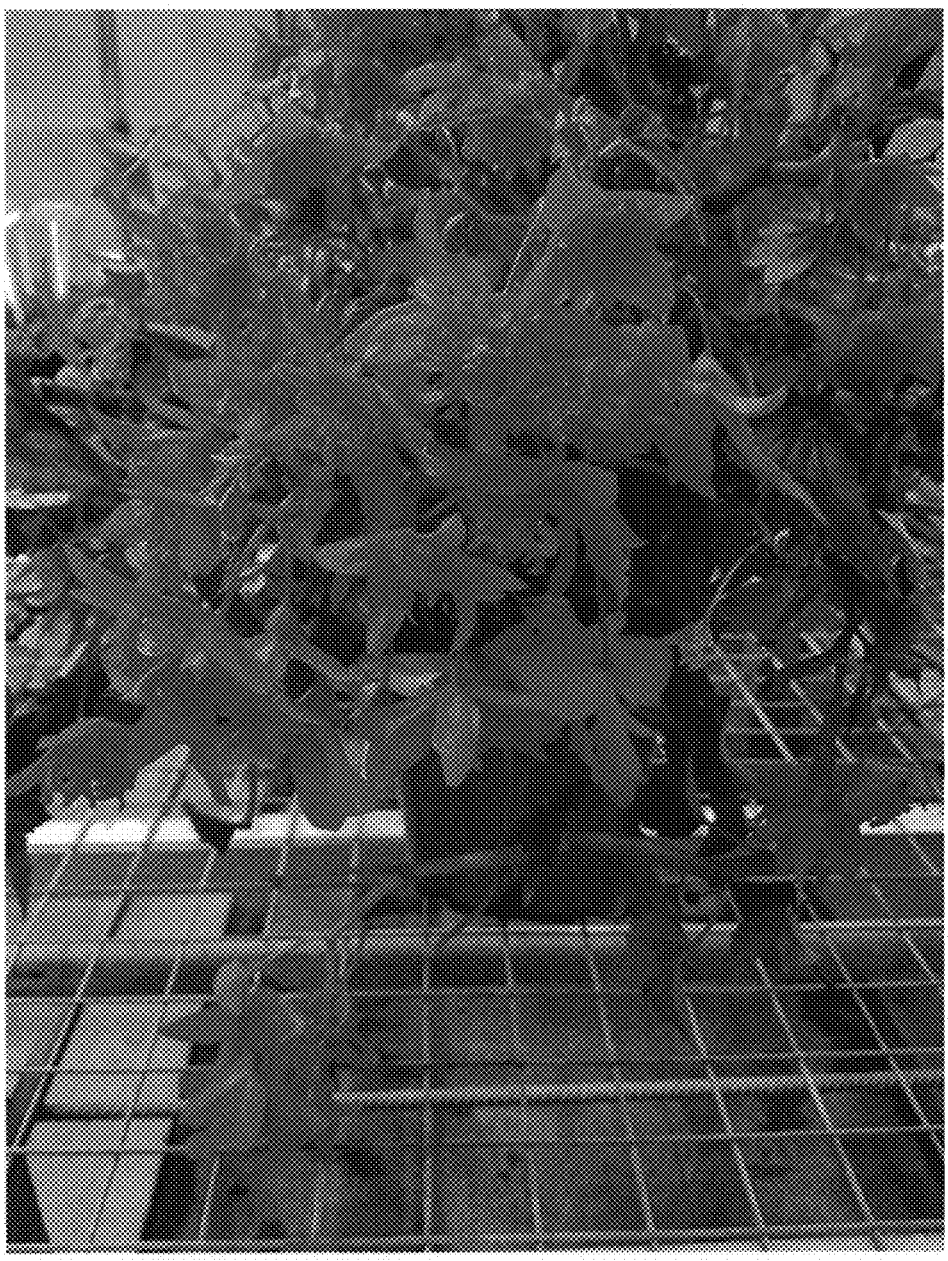
FIG. 2 shows a plant that is 7 to 8 months old grown in a greenhouse in Stuttgart, Germany in October 2017.
Figure 3:
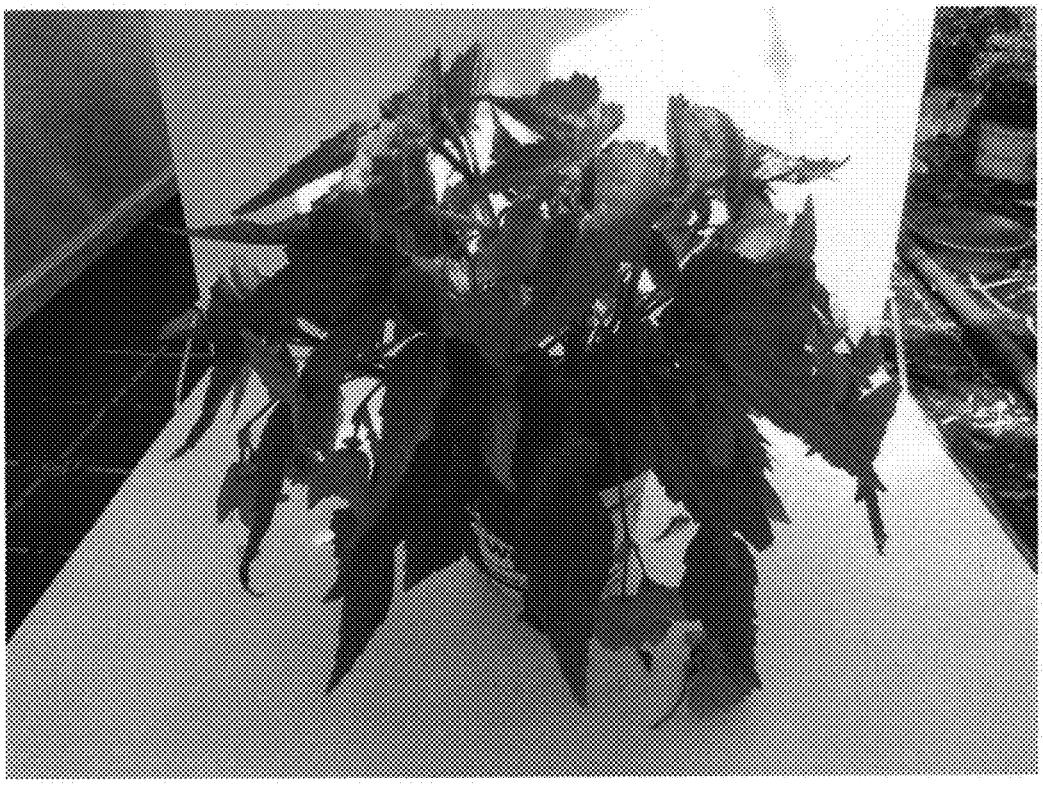
FIG. 3 shows a plant that is two months old grown in a greenhouse in Stuttgart, Germany in May 2017.

The following detailed descriptions set forth the distinctive characteristics of 'KLEBG15006'. The data which define these characteristics were collected from asexual reproductions carried out in Stuttgart, Germany. Data was collected on two month-old plants grown in a greenhouse in Stuttgart, Germany in March and April 2016. Plants were grown with natural light, pinched one time, and grown with no growth regulators. Color references are to The R.H.S. Colour Chart of The Royal Horticultural Society of London (R.H.S.), 5th edition (2007).

Classification:

*Family*.—Begoniaceae.

*Species*.—*Begonia* spp.

*Common name*.—*Begonia*.

*Variety*.—'KLEBG15006'.

Parentage:

*Female*.—'BG-2010-0090' (unpatented).

*Male*.—'BG-2010-0068' (unpatented).

Plant description:

*Plant form*.—Semi-trailing.

*Plant habit*.—Bushy, freely branching.

*Plant height*.—10 cm.

*Plant width*.—25 cm.

*Flowering habit*.—Monoecious, producing both male and female flowers on the same plant, double male, single female flowers.

*Time to produce a finished flowering plant*.—2 to 3 months.

*Propagation type*.—Vegetative stem tip cuttings.

*Time to initiate roots*.—Approximately 2 weeks.

*Root description*.—Freely branching, fibrous, light tan in color.

Lateral branches:

*Quantity*.—4 to 6 basal branches.

*Color*.—RHS 144B.

*Length*.—3.0 cm to 5.0 cm.

*Diameter*.—0.5 cm to 1.0 cm.

*Internode length*.—1.0 cm.

*Texture*.—Covering of fine colorless hairs.

*Anthocyanin*.—Some present on upper nodes, RHS 180C.

Foliage description:

*Arrangement*.—Alternate.

*Length*.—Up to 11.0 cm.

*Width*.—4.0 cm to 5.0 cm.

*Shape*.—Lanceolate, strongly asymmetric with one side ovate.

*Apex*.—Acuminate.

*Base*.—Oblique cordate.

*Margin*.—Serrate with short bristles emerging from tips of the teeth.

*Texture*.—Smooth upper surface; lower surface sparsely covered with hairs.

*Color*.—Immature leaves: Upper surface: RHS 141B with anthocyanin RHS 183B around veins. Lower surface: RHS 141C with anthocyanin RHS 184B. Mature leaves: Upper surfaces: RHS 141B. Lower surface: RHS 141C.

*Venation pattern*.—Pinnate and Palmate.

*Venation color*.—Upper surface: Between RHS 141B and RHS 141C. Lower surface: Between RHS 141C and RHS 141D.

*Petiole*.—Length: Up to 6.0 cm. Diameter: 0.3 cm. Color: RHS 145A; tendency to anthocyanin RHS 182C. Texture: Covering of fine colorless hairs.

Flower description:

*Flower type*.—Single and double flowers arranged in axillary cymes.

*Quantity of flowers per cyme*.—1 to 2.

*Quantity of cymes per plant*.—Approximately 8.

*Natural flowering season*.—Spring to autumn.

*Lastingness of individual flowers on the plant*.—1 to 2 weeks.

*Fragrance*.—Absent.

*Bracts*.—Quantity per flower: 2. Length: 1.2 cm. Width: 1.0 cm. Shape: Round to ovate. Apex: Acute. Base: Rounded. Margin: Entire. Color (both surfaces): RHS 145A, apex RHS 47C.

*Peduncle*.—Length: 5.0 cm. Diameter: 0.2 cm. Color: RHS 144C with RHS 180D anthocyanin. Texture: Smooth.

*Female flowers*.—Bud: Shape: Flattened ovate. Height: Approximately 2.0 cm. Width: Approximately 1.5 cm. Color: RHS 32B. Texture: Smooth. Flowers: Shape: Single, radial bell-mouthed. Depth/Height: 2.0 cm. Width: 3.0 cm to 5.0 cm. Tepals (both outer and inner): Quantity per flower: 3 outer and 2 inner. Shape: Ovate. Length: 2.0 cm. Width: 1.2 cm. Apex: Acute. Base: Fused. Color upper surface: RHS 32A. Color lower surface: RHS 32A and RHS 32B, base lighter. Texture: Smooth. Pedicel: Length: 3.0 cm. Diameter: 0.1 cm. Color: RHS 144C with RHS 180D anthocyanin. Texture: Smooth.

*Male flowers*.—Shape: Double, rounded. Depth/Height: 2.0 cm. Width: 6.0 cm. Tepals: Rosette-like arrangement. Tepal quantity per flower: Approximately 8 outer and 40 smaller inner tepals. Inner tepals: Shape: Ovate to elliptical. Length: 0.5 cm to 1.5 cm. Width: 0.5 cm to 1.0 cm. Apex: Broad acute. Base: Fused. Color upper surface: RHS 32A. Color lower surface: RHS 32A and RHS 32B, base and middle lighter. Texture: Smooth. Outer tepals: Shape: Ovate to elliptical. Length: 3.0 cm. Width: 2.0 cm. Apex: Broad acute. Base: Fused. Color upper surface: RHS 32A. Color lower surface: RHS 32A and RHS 32B, base lighter. Texture: Smooth. Pedicel: Length: 2.0 cm. Diameter: 0.2 cm. Color: RHS 144C with RHS 180D anthocyanin. Texture: Smooth.

Reproductive organs:

*Stamens* (*on the male flowers*).—Androecium absent.

*Pollen*.—Absent.

*Pistils* (*on the female flowers*).—Quantity per flower: 3. Pistil length: 1.5 cm. Style length: 0.5 cm (including extensions). Style color: RHS 30B. Stigma shape: Bifid, twisted around extensions of the style. Stigma color: RHS 17A. Ovary color: RHS 145A.

Fruit and seed: None observed.

Disease and insect/pest resistance: No special observations were made.

COMPARISON WITH PARENTAL LINES AND KNOWN VARIETY

'KLEBG15006' is a distinct variety of *Begonia*. 'KLEBG15006' is distinguished from its parents as described in Table 1:

TABLE 1

Comparison with Parental Lines

| Trait | Variety 'KLEBG15006' | Female parent 'BG-2010-0090' | Male parent 'BG-2010-0068' |
|---|---|---|---|
| Flower color | Orange-red | Red | Salmon-orange |

'KLEBG15006' is most similar to the commercial *Begonia* plant named 'KLEBG13465' (U.S. Plant Pat. No. 26,809), also known as 'California Sunlight'. Differences between the two varieties are described in Table 2:

TABLE 2

Comparison with Similar Variety

| Trait | Variety 'KLEBG15006' | Commercial line 'KLEBG13465' |
|---|---|---|
| Flower type | Double male flowers and single female flowers | Single male and female flowers |

We claim:

1. A new and distinct variety of *Begonia* plant named 'KLEBG15006' as illustrated and described herein.

* * * * *